US011766496B2

(12) United States Patent
Konya et al.

(10) Patent No.: US 11,766,496 B2
(45) Date of Patent: Sep. 26, 2023

(54) ANTIMICROBIAL FABRIC FRESHENING COMPOSITIONS CONTAINING OCTENIDINE DIHYDROCHLORIDE

(71) Applicant: The Procter & Gamble Company, Cincinnati, OH (US)

(72) Inventors: Abigail Mary Konya, Newcastle upon Tyne (GB); Eva Maria Perez-Prat Vinuesa, Durham (GB)

(73) Assignee: The Procter & Gamble Company, Cincinnati, OH (US)

( * ) Notice: Subject to any disclaimer, the term of this patent is extended or adjusted under 35 U.S.C. 154(b) by 414 days.

(21) Appl. No.: 16/923,199

(22) Filed: Jul. 8, 2020

(65) Prior Publication Data

US 2021/0030910 A1 Feb. 4, 2021

(30) Foreign Application Priority Data

Jul. 29, 2019 (EP) .................................... 19188859

(51) Int. Cl.
| | | |
|---|---|---|
| *C11D 1/62* | (2006.01) | |
| *A61L 9/01* | (2006.01) | |
| *A61L 9/14* | (2006.01) | |
| *C11D 3/00* | (2006.01) | |
| *C11D 3/48* | (2006.01) | |
| *C11D 3/50* | (2006.01) | |
| *C11D 3/30* | (2006.01) | |

(52) U.S. Cl.
CPC .................................... *A61L 9/01* (2013.01); *A61L 9/14* (2013.01); *C11D 3/0068* (2013.01); *C11D 3/48* (2013.01); *C11D 3/50* (2013.01); *A61L 2202/26* (2013.01); *A61L 2209/21* (2013.01); *C11D 3/30* (2013.01)

(58) Field of Classification Search
CPC .. C11D 1/62; C11D 1/835; C11D 1/82; C11D 3/43; C11D 3/48; C11D 3/50; C11D 7/5077; C11D 9/44; C11D 11/0017; C11D 17/0043
See application file for complete search history.

(56) References Cited

U.S. PATENT DOCUMENTS

| | | | |
|---|---|---|---|
| 3,892,681 A | | 7/1975 | Edwards et al. |
| 5,468,423 A | * | 11/1995 | Garabedian, Jr. ...... C11D 3/044 510/423 |
| 5,578,563 A | | 11/1996 | Trinh |
| 10,513,671 B2 | | 12/2019 | Lant |
| 2003/0216282 A1 | * | 11/2003 | Martens .................... C11D 3/40 510/521 |
| 2013/0149367 A1 | * | 6/2013 | Messier .................. A01N 59/12 424/404 |
| 2013/0177518 A1 | * | 7/2013 | Nielsen .................. C11D 1/835 514/634 |
| 2015/0217015 A1 | * | 8/2015 | Williams ............. C11D 3/0068 424/76.21 |
| 2016/0017262 A1 | * | 1/2016 | Mønster .................. A01N 25/02 514/634 |
| 2016/0177518 A1 | | 6/2016 | Bletscher |
| 2017/0188578 A1 | * | 7/2017 | Gundlapalli ......... A61K 8/0208 |
| 2017/0274111 A1 | * | 9/2017 | Nwachukwu ............. A61L 9/01 |
| 2021/0032806 A1 | | 2/2021 | Wilkinson et al. |
| 2021/0298303 A1 | * | 9/2021 | Stadler ...................... A23L 2/44 |
| 2022/0174958 A1 | * | 6/2022 | Fellows ................. A01N 33/12 |

FOREIGN PATENT DOCUMENTS

| | | |
|---|---|---|
| EP | 2443925 B1 | 11/2014 |
| EP | 2443924 B1 | 6/2016 |
| WO | WO2018108466 A1 | 6/2018 |

OTHER PUBLICATIONS

EP Search report for Appl. No. 19188859.3-1107, dated Feb. 21, 2020, 8 pages.
EP Search report for appl. No. 19188864.3-1105, dated Feb. 3, 2020, 6 pages.
International Search Report and Written Opinion; Application Ser. No. PCT/US2020/070287; dated Oct. 9, 2020; 11 pages.

* cited by examiner

*Primary Examiner* — Charles I Boyer
(74) *Attorney, Agent, or Firm* — Andrew J. Mueller

(57) ABSTRACT

A fabric freshening product that includes (a) freshening aqueous liquid composition including a bispyridinium alkane antimicrobial active and a perfume, and (b) a spray device to produce a spray of the composition.

16 Claims, No Drawings

ANTIMICROBIAL FABRIC FRESHENING COMPOSITIONS CONTAINING OCTENIDINE DIHYDROCHLORIDE

FIELD OF THE INVENTION

The present invention relates to a fabric freshening product comprising a composition having a bispyridinium alkane antimicrobial active and a spray device to spray the composition.

BACKGROUND OF THE INVENTION

Freshening products for freshening fabrics or reducing/eliminating malodors on fabrics are currently available. These products typically contain a freshening composition that includes perfume raw materials (PRMs), solvents, surfactants, and high levels of water. Having a wide variety of scent choices in freshening products enables consumers to find one that they like.

However, because of the hydrophobic nature of PRMs, surfactants and/or solvents are used to solubilize and emulsify the PRMs, especially given formulations with high levels of water. However, solvents and relatively high levels of surfactants, although help to emulsify particularly hydrophobic PRMs, may pose at least one of several challenges.

For example, although surfactants are used, the levels are to be minimized otherwise the surfactants may cause fabrics or surfaces to turn yellow or brown under natural light and/or make fabric or surfaces susceptible to soiling and/or change the consumer perception of how the fabric or surface feels. Solvent selection and levels are to be considered as they have limited ability to solubilize a wide range of PRMs, have environmental considerations, and may negatively impact scent. Additionally, many solvents used are high Volatile Organic Compounds (VOC). VOC materials pose challenges for negatively impacting scent as well as concerns around flashpoint regulations. Given these challenges, formulators typically have solvent and surfactant limitations, which in turn minimizes the use of relatively more hydrophobic PRMs. This reduces the breadth of available PRMs and thus scent experiences to users. These challenges are exacerbated when formulations contain especially high levels of water and/or high levels of relatively hydrophobic PRMs.

It is desirable that freshening compositions not only perfume the fabrics but also provide sanitizing of the fabric.

Quaternary ammonium compounds are highly effective antibacterial actives commonly used in household products such as surface cleaners; however, quaternary ammonium compounds are not a good choice for fabric freshener compositions. Quaternary ammonium compounds can interact with the surfactants needed to solubilize the perfume in the fabric freshener compositions, as a result of this interaction, the antimicrobial efficacy of the composition is reduced, or else, high levels of the quaternary ammonium must be used. The use of high levels of quaternary ammonium antibacterial actives is not desirable for environmental reasons.

Alkylamines are also known for their antibacterial properties. These compounds are not a good choice for fabric freshener compositions because they have a very unpleasant amine-like odour that is very difficult to mask and can react with aldehyde PRMs changing the perfume character and/or decreasing its intensity.

Therefore, there is a need for freshening compositions that provide antimicrobial benefits with low levels of antimicrobial active, without impacting the perfume character and intensity and without staining fabrics.

SUMMARY OF THE INVENTION

The present disclosure relates to a fabric freshening product. The product comprises a freshening composition and a spray device. The freshening composition comprises a bispyridinium alkane antimicrobial active and a perfume. The composition is an aqueous liquid composition and preferably comprises surfactant and solvent and preferably a malodour counteractant and/or a setting polymer and/or an anti-wrinkle agent. The composition is a Newtonian liquid.

The present disclosure also relates to a method of freshening and sanitizing a fabric using the product as described herein.

DETAILED DESCRIPTION OF THE INVENTION

The product of the present disclosure comprises a composition. The composition comprises a bispyridinium alkane antimicrobial active and a perfume. The perfume comprises perfume raw materials (PRMs). PRMs are typically formulated with water to make sprayable fabric freshening compositions. However, because of the hydrophobic nature of PRMs, solvents and/or surfactants are used to solubilize and emulsify the PRMs in compositions with high water content. Solvents suitable for solubilizing PRMs typically include alcohols, polyols and mixtures thereof.

The present disclosure relates to the surprising discovery that freshening composition comprising low levels of bispyridinium alkanes can provide fabric sanitization.

In the following description, the composition described is a fabric freshening composition.

Prior to describing the present invention in detail, the following terms are defined for clarity. Terms not defined should be given their ordinary meaning as understood by a skilled person in the relevant art.

The term "freshening composition" as used herein refers to compositions for providing freshness on fabrics.

As used herein, the terms "microbe" or "microbial" should be interpreted to refer to any of the microscopic organisms studied by microbiologists or found in the use environment of a treated surface. Such organisms include, but are not limited to, bacteria and fungi as well as other single-celled organisms such as mould, mildew and algae. Viruses (enveloped and non-enveloped) and other infectious agents are also included in the term microbe.

"Antimicrobial" further should be understood to encompass both microbiocidal and microbiostatic properties. That is, the term includes microbe killing, leading to a reduction in number of microbes, as well as a retarding effect of microbial growth, wherein numbers may remain more or less constant (but nonetheless allowing for slight increase/decrease).

For ease of discussion, this description uses the term antimicrobial to denote a broad-spectrum activity (e.g. against bacteria and fungi, or against bacteria and viruses). When speaking of efficacy against a particular microorganism or taxonomic rank, the more focused term will be used (e.g. antifungal to denote efficacy against fungal growth in particular). Using the above example, it should be understood that efficacy against fungi does not in any way preclude the possibility that the same antimicrobial composition may demonstrate efficacy against another class of microbes.

The term "Perfume Raw Materials" as used herein refer to perfume materials ("PRMs" or, singularly, "PRM").

The term "C log P" as used herein refers to a calculated log P ("C log P") value of a PRM. An octanol/water partition coefficient of a PRM is the ratio between its equilibrium concentrations in octanol and in water. The partition coefficients of the PRM used in a freshening composition may more conveniently be given in the form of its logarithm to the base 10, Log P. The C log P is determined by a model that computes the octanol-water partition coefficient (log P or log Kow) for general organic molecules based directly on molecular structure. Log P is a measure of the distribution of a solute between two immiscible liquid phases, octanol and water, and is generally used as a relative measure of the hydrophobicity of a solute. One way of computing Log P of a PRM is using the ACD/Labs Log P software module from Advanced Chemistry Development, Inc. Details of the calculation of log P can be found on the ACD/Labs website (https://www.acdlabs.com/products/percepta/predictors/logp/). Log P values of PRMs calculating using the ACD/Labs Log P software module and the Log P values of PRMs are used in the selection of PRMs which are useful in the present invention as described hereafter in the Examples. However, it will be appreciated that another suitable way of measuring Log P is using the "C log P" program from BioByte Corp (e.g., C log P Version 4.0 and Manual 1999). CLOG P USER GUIDE, Version 4.0, BioByte Corp (1999) (http://www.bio-byte.com/bb/prod/clogp40.html). A further suitable way of measuring Log P is using C LOG P program from Daylight Chemical Information Systems, Inc. of Alison Viejo, Calif. The C LOG P Reference manual, Daylight Version 4.9, Release Date Feb. 1, 2008.

The term "sulfur-containing pro-perfume" as used herein refers to a type of pro-perfume compound that contains sulfur. The term "pro-perfume" as used herein refers to compounds resulting from the reaction of PRMs with other chemicals, which have a covalent bond between one or more PRMs and these chemicals. The PRM is converted into a new material called a pro-perfume compound, which then may release the original PRM (i.e. pre-converted) upon exposure to a trigger such as water or light or atmospheric oxygen. Suitable pro-perfume compounds and methods of making the same can be found in U.S. Pat. Nos. 7,018,978; 6,861,402; 6,544,945; 6,093,691; 6,165,953; and 6,096,918.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

Freshening Composition

A freshening composition according to the present invention comprises a bispyridinium alkane antimicrobial active, preferably octenidine dihydrochloride, in a level of at least 0.001% to 1%, preferably from 0.05% to 0.8%, more preferably from 0.06% to 0.7% by weight of the composition, and a perfume wherein the perfume preferably comprises at least 60% by weight of perfume, of PRMs having a C log P greater than 1. The composition is an aqueous liquid composition comprising at least 90%, preferably at least 95% and more preferably at least 98% and less than 99.5% of water by weight of the composition. Having high levels of water enable a sprayable freshening composition while minimizing any visible residues and/or stains on fabric articles. The Newtonian fluid of the invention preferably has a viscosity of from 1 cps to 500 cps, more preferably of from 1 cps to 300 cps, more preferably from 1 cps to 200 cps, even more preferably from 1 cps to 100 cps and most preferably from 1 cps to 50 cps and especially for 1 cps to 20 cps when measured at 20° C. with a AD1000 Advanced Rheometer from Atlas® shear rate 10 s−1 with a coned spindle of 40 mm with a cone angle 2° and a truncation of ±60 μm. The freshening composition is sprayable and the perfume remains solubilized to provide a phase-stable freshening composition that provides a consistent delivery of scent freshness in each spray.

Components of a freshening composition of the present invention are described in the following paragraphs.

Antimicrobial Agent

The composition of the invention comprises bispyridinium alkanes, such as the ones described in GB1533952. The term bispyridinium alkane comprises the bis[4-(substituted-amino)-1-pyridinium]alkanes of the general formulae (I) or (II)

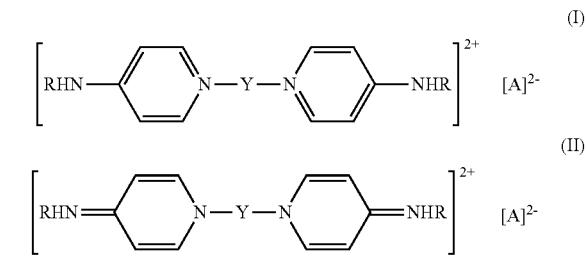

in which

Y is an alkylene or alkyl group having 4 to 18 carbon atoms,

R represents an alkyl group having 6 to 18 carbon atoms or a cycloalkyl group having 5 to 7 carbon atoms or a phenyl group with or without halogen substitution, and A is an anion or several anions.

A may be a monovalent, divalent or a polyvalent anion, for example chloride, bromide, phosphate or orthosilicate. A may also be an organic acid having the formula R4-COO~, wherein R4 is hydrogen, hydroxyl, or C1-C40 alkyl.

Bispyridinium alkanes of the present invention comprise the various prototypes of the compounds of the formula (I) and (II) such as, for example, the ones disclosed in GB1533952 and DE19647692A1.

Other suitable bispyridinium alkanes comprise an organic acid salt of a bispyridine amine where the organic acid contains from about 4 to about 30 carbon atoms, such as, for example, the ones described in WO2014100807. Suitable organic acids include but are not limited to, carboxylic acids, such as (C1-C40) alkanecarboxylic acids which, for example, are unsubstituted or substituted by halogen, saturated or unsaturated dicarboxylic acids, such as hydroxycarboxylic acids, such as amino acids, such as (C1-C40) alkylsulfonic acids. Additional organic acids from which salts can be derived include, for example, acetic acid, propionic acid, phosphoric acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, glycyrrhizinic acid, salicylic acid, stearic acid, phosphonic acid, trifluoroacetic acid, cyanoacetic acid, 4-cyanobenzoic acid, 2-chlorobenzoic acid, 2-nitrobenzoic acid, phenoxyacetic acid, benzenesulfonic acid. Preferred are salts of stearate such as bispyridinium alkane distearate.

Preferred bispyridinium alkane is octenidine dihydrochloride (R=n-octyl, Y=n-decenyl; A=2×Cl, hereinbelow "octenidine" CAS number 70775-75-6).

The antimicrobial agent need only be present in germicidally effective amounts, which can be as little as 0.001 wt % to less than 1% by weight of the composition. In more preferred compositions, the cleaning composition comprises the antimicrobial agent at a level of from about 0.0025 to about 0.5%, more preferably from 0.005% to 0.15% by weight of the composition.

Quaternary Ammonium Compounds

The composition of the invention may comprise a quaternary ammonium compound or may be substantially free of quaternary ammonium compounds. By "substantially free" of quaternary ammonium antimicrobial active is herein meant that the composition comprises less than 0.001% by weight of the composition of quaternary ammonium antimicrobial active.

Quaternary ammonium compounds include compounds of formula (A):

wherein $R^1$ and $R^2$ are each independently a straight chain, unsubstituted and uninterrupted $C_8$-$C_{12}$ alkyl group and $X^-$ is a halide anion such as chloride, bromide, fluoride, iodide or sulphonate, saccharinate, carbonate or bicarbonate, and benzalkonium compounds having the formula (B)

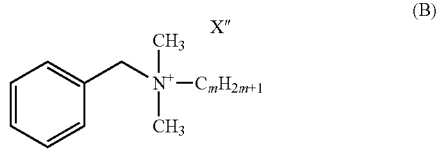

wherein m is from 8 to 18, and $X^-$ is a halide anion such as chloride, bromide, fluoride, iodide, sulphonate, saccharinate, carbonate or bicarbonate. This benzalkonium compounds usually comprise a mixture of $C_8$-$C_{18}$ alkyl groups, particularly a mixture of straight chain, unsubstituted and uninterrupted alkyl groups such as n-$C_8H_{17}$ to n-$C_{18}H_{37}$, mainly n-$C_{12}H_{25}$ (dodecyl), n-$C_{14}H_{29}$ (tetradecyl), and n-$C_{16}H_{33}$ (hexadecyl).

In the compounds of formula (A) each group $R^1$ and $R^2$ is independently a straight chain, unsubstituted, uninterrupted $C_{8-12}$ alkyl group, for example an alkyl group containing 8, 9, 10, 11 or 12 carbon atoms. The groups $R^1$ and $R^2$ may contain equal or different numbers of carbon atoms.

Examples of quaternary ammonium compounds of formula (A) include di-n-decyldimethyl ammonium chloride, octyl decyl dimethyl ammonium chloride and dioctyl dimethyl ammonium chloride.

Examples of quaternary ammonium compounds of formula (B) include N,N-benzyldimethyloctylammonium chloride, N,N-benzyldimethyldecylammonium chloride, N-dodecyl-N-benzyl-N,N-dimethylammonium chloride, and N-tetradecyl-N-benzyl-N,N-dimethylammonium chloride, N-hexadecyl-N,N-dimethyl-N-benzylammonium chloride.

Perfume Composition (Hereinafter "Perfume")

The freshening composition comprises a perfume formulated in an effective amount such that it provides a desired scent characteristic and can be homogenously solubilized in the freshening composition to deliver a consistent release profile. The perfume preferably comprises at least 60% by weight of the perfume of Perfume Raw Materials (PRMs) having a C log P value greater than 1.0. The perfume may be in an amount of at least 0.001%, from 0.002% to 3%, from 0.005% to 1%, from 0.005% to 0.4% by weight of the composition. Suitable perfumes, perfume ingredients, and perfume carriers are disclosed in U.S. Pat. No. 5,500,138 and U.S. Publication No. 2002/0035053A1.

Any type of perfume can be incorporated into the composition of the present invention. The preferred perfume ingredients are those suitable for use for application on fabrics and garments. Typical examples of such preferred ingredients are given in U.S. Pat. No. 5,445,747.

The PRMs may be defined by their boiling point ("B.P.") and octanol/water partition coefficient ("P"). The boiling point referred to herein is measured under normal standard pressure of 760 mmHg. The boiling points of many PRMs, at standard 760 mm Hg, are outlined in "Perfume and Flavor Chemicals (Aroma Chemicals)," written and published by Steffen Arctander, 1969.

When long lasting fragrance odor on fabrics is desired, it is preferred to use at least an effective amount of perfume ingredients which have a boiling point of about 240° C. or higher and preferably of about 250° C. or higher. Nonlimiting examples of such preferred ingredients are given in U.S. Pat. No. 5,500,138.

Other perfume ingredients can act as solvents. In some cases this can help facilitate the incorporation of other perfume or oil ingredients into the overall composition. A particularly good example here is benzyl alcohol. Benzyl alcohol has limited water solubility (c log P of about 1.2) and has been shown to help incorporate other perfume ingredient mixes into these compositions.

Sulfur-Containing Pro-Perfume

The freshening composition may comprise a sulfur-containing pro-perfume. A technical effect of the sulfur-containing pro-perfume is that it improves the stability of freshening compositions. The sulfur-containing pro-perfume compound may be present at various levels in the composition. Specifically, the freshening composition may comprise from about 0.001% to about 5%, alternatively from about 0.001% to about 3%, alternatively from about 0.01% to about 1%, alternatively about 0.01% to about 0.5%, alternatively about 0.01% to about 0.1%, alternatively at least about 0.02%, or different combinations of the upper and lower percentages described above or combinations of any integer in the ranges listed above of a sulfur-containing pro-perfume by weight of the freshening composition.

The freshening composition may comprise dodecyl thiodamascone having the general structure shown below.

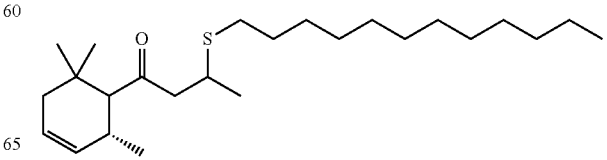

Thio-damascone may be present in an amount form about 0.001% to about 1.0%, alternatively from about 0.001% to about 5.0%, alternative from about 0.001% to about 3.0%, alternatively from about 0.01% to about 1.0%, alternatively about 0.01% to about 0.5%, alternative about 0.01% to about 0.1%, alternatively at least about 0.02% by weight of the freshening composition.

The weight ratio of perfume mixture to sulfur-containing pro-perfume may be about 0.01:1 to about 200:1, or about 5:1 to about 50:1, or about 10:1 to about 40:1, or about 10:1 to about 20:1, by weight of the composition.

Solvents

The freshening composition may comprise a solvent for solubilizing the perfume. Specifically, the composition may comprise less than 10%, from 0.01% to 5%, from 0.01% to 3%, from 0.01% to 1%, from 0.01% to 0.05% by weight of the freshening composition. The solvent may be selected from a group consisting of: an alcohol, a polyol and mixtures thereof. The solvent may comprise low molecular weight monohydric alcohols (e.g., ethanol, methanol, and isopropanol, or polyols, such as ethylene glycol and propylene glycol).

Alkoxylated Phenol

The freshening composition might comprise an alkoxylated phenol in a level of at least 0.0015% by weight of the composition. Without wishing to be bound by theory, use of alkoxylated phenols relative to use of traditional solvents such as ethanol to solubilize perfumes in freshening compositions is alkoxylated phenols have the combination of a phenol functional group and an ether functional group in the same molecule which provides unique solvency characteristics with both polar and non-polar properties. This surfactant-like structure gives alkoxylated phenols the ability to couple unlike liquid phases of ingredients used for freshening compositions (e.g. water and perfume as described hereinafter) and be miscible in a broad range of hydrophilic and hydrophobic solvents.

Surfactants

The freshening composition may contain a surfactant to solubilize any excess hydrophobic organic materials, particularly any PRMs, and also optional ingredients (e.g., insect repelling agent, antioxidant, etc.) which can be added to the composition, that are not readily soluble in the composition, to form a clear solution. The freshening composition may comprise less than 3.5%, from 0.01% to 3%, from 0.01% to 1%, from 0.01% to 0.05% by weight of the freshening composition. A suitable surfactant is a no-foaming or low-foaming surfactant. The surfactant may be selected from the group consisting of: nonionic surfactants, cationic surfactants, amphoteric surfactants, zwitterionic surfactants and mixtures thereof.

Malodor Binding Polymer

The freshening composition of the present invention may comprise a malodor binding polymer. A malodor binding polymer is polymer having an available functional group (e.g. amine) that has the affinity to neutralize malodor components. Monomers having an available function group with an affinity to neutralize malodor components are also contemplated. In the case of amine based compounds, the amine will have an affinity for aldehyde malodors. The amine may react with aldehyde malodors and form a new compound, such as an aminol, imine, or enamine which is not odorous.

A malodor binding polymer may include amine based compounds, such as monoamines, amino acids, polyethyleneimine polymers (PEIs), modified PEIs, substituted PEIs; acrylic acid polymers, such as polyacrylate co-polymer (e.g. Acumer™ 9000 from Rohm & Haas), polyacrylic acid polymers (e.g. Acusol™ from Rohm & Haas), and modified acrylate copolymers (e.g. Aculyn™ from Rohm & Haas); and modified methacrylate copolymers (e.g. HydroSal™ from Salvona Technologies); or mixtures thereof.

Suitable levels of malodor binding polymer are from about 0.01% to about 2%, alternatively from about 0.01% to about 1%, alternatively about 0.01% to about 0.8%, alternatively about 0.01% to about 0.6%, alternatively about 0.01% to about 0.1%, alternatively about 0.01% to about 0.07%, alternatively about 0.07%, by weight of the freshening composition. Compositions with higher amount of malodor binding polymer may make fabrics susceptible to soiling and/or leave unacceptable visible stains on fabrics as the solution evaporates off of the fabric.

Malodor Counteractant

The freshening composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces. For example, aliphatic aldehydes react with amine odors, such as fish and cigarette odors. When used in combination with the malodor binding polymer, the freshening composition may neutralize a broader range of malodor causing materials which, in turn, further reduces malodors in the air or on inanimate surfaces.

Specifically, the freshening composition may include a malodor counteractant, wherein the malodor counteractant is selected from the group consisting of: polyols, cyclodextrin and derivatives thereof, amine functional polymers, aldehydes, and combinations thereof. The malodor counteract may be cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

Buffering System

The freshening composition may include a buffering agent. The buffering agent may be an acidic buffering agent. The buffering agent may be a dibasic acid, carboxylic acid, dicarboxylic acid such as maleic acid, tricarboxylic acid such as citric acid, or a polycarboxylic acid such as polyacrylic acid. The carboxylic acid may be, for example, citric acid, polyacrylic acid, or maleic acid. The acid may be sterically stable. The acid may be used in the composition for maintaining the desired pH. The freshening composition may have a pH from about 4 to about 9, alternatively from about 4 to about 8.5, alternatively from about 4 to about 6.9, alternatively about 4 to about 6.7. Preferably, the buffer system comprises one or more buffering agents selected from the group consisting of: citric acid, maleic acid, polyacrylic acid, and combinations thereof. It has been found that buffer systems that include a buffering agent selected from the group consisting of: citric acid, maleic acid, polyacrylic acid, and combinations thereof provide stable freshening compositions with prolonged shelf life.

Preferably, the buffer system comprises citric acid and sodium citrate. It has been found that buffer systems comprising citric acid and sodium citrate provide stable freshening compositions with a prolonged shelf life.

The freshening compositions may include a secondary or tertiary amine. The freshening compositions may contain at least about 0%, alternatively at least about 0.001%, alternatively at least about 0.01%, by weight of the composition, of a buffering agent. The composition may also contain no more than about 2%, alternatively no more than about 0.75%, alternatively no more than about 0.5%, by weight of the composition, of a buffering agent.

Wetting Agent

The freshening composition may include a wetting agent that provides a low surface tension that permits the composition to spread readily and more uniformly on hydrophobic surfaces like polyester and nylon. It has been found that the freshening composition, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated freshening compositions. Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic™ and Tetronic™ by the BASF-Wyandotte Corp., Wyandotte, Mich., are readily available.

Another suitable wetting agents that can be used in the present composition are the SILWET silicone polyethers. Nonlimiting examples of these silicone polyethers include the SILWET™ surfactants available from Momentive Performance Chemical, Albany, N.Y. Exemplary SILWET™ surfactants are as follows in Table 6 below. However, it will be appreciated that mixtures of the following surfactants may also be used in the present invention.

TABLE 6

| SILWET ™ Surfactants | Average MW |
| --- | --- |
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |

The total amount of surfactants (e.g. solubilizer, wetting agent) in the freshening composition is from 0 to about 3%, alternatively from 0 to about 1%, alternatively from 0 to about 0.9%, alternatively from to about 0.7%, alternatively from 0 to about 0.5%, alternatively from 0 to 0.3% by weight of the composition. Compositions with higher concentrations can make fabrics susceptible to soiling and/or leave unacceptable visible stains on fabrics as the solution evaporates.

Setting Polymers

The composition of the present invention may further comprise one or more setting polymers, "setting polymer" means any polymer which refers to polymer having properties of film-formation, adhesion, or coating deposited on a surface on which the polymer is applied The setting polymer may be present at a level from about 0.5% to about 5%, by weight of the garment refreshing composition. The molecular weight of the setting polymer is preferably from 1,000 to 500,000, more preferably from 2,000 to 250,000 even more preferably from 5,000 to 200,000.

The setting polymer according to the present invention may be any water-soluble or water dispersible polymer. Preferably the polymer is a film-forming polymer or mixture of such polymers. This includes homopolymers or copolymers of natural or synthetic origin having functionality rendering the polymers water-soluble such as hydroxyl, amine, amide or carboxyl groups. The setting polymers may be cationic, anionic, non-ionic or amphoteric. The polymers make be a single species of polymer or a mixture thereof. Preferably the setting polymer is selected from: anionic polymers, non-ionic polymers, amphoteric polymers and mixtures thereof.

Anti-Wrinkle Agent

The compositions of the present invention may optionally comprise an anti-wrinkle agent which may comprise silicone and preferably this is in an emulsion. Silicone may be present at a level from about 0.5% to about 6%, by weight of the composition.

Freshening Product

The freshening product comprises a spray dispenser. The spray dispenser may be transparent or translucent such that the freshening composition is visible or at least partially visible from outside of the freshening product.

The spray dispenser may hold various amounts of freshening composition. The spray dispenser may be capable of withstanding internal pressure in the range of about 20 p.s.i.g. to about 140 psig, alternatively about 80 to about 130 p.s.i.g. The total composition output and the spray droplet/particle size distribution may be selected to support the particulate removal efficacy but avoid a surface wetness problem. Total output is determined by the flow rate of the composition as it is released from the spray dispenser. To achieve a spray profile that produces minimal surface wetness, it is desirable to have a low flow rate and small 5 spray droplets.

The flow rate of the composition being released from the spray dispenser may be from about 0.0001 grams/second (g/s) to about 2.5 grams/second. Alternatively, the flow rate may be from about 0.001 grams/second to about 2.5 grams/second, or about 0.01 grams/second to about 2.0 grams/second. For an aerosol sprayer, the flow rate is determined by measuring the rate of composition expelled by a spray dispenser for any 60 second period of use.

The Sauter Mean Diameter of the spray droplets may be in the range of from about 10 μm to about 100 μm, alternatively from about 20 μm to about 60 μm. At least some of the spray droplets are sufficiently small in size to be suspended in the air for at least about 10 minutes, and in some cases, for at least about 15 minutes, or at least about 30 minutes. Small particles can be efficiently created when the spray is dispensed in a wide cone angle. For a given nozzle component and delivery tube, cone angles can be modified by varying the insertion depth of the nozzle in the delivery tube. The cone angle may be greater than about 20 degrees, or greater than about 30 degrees, or greater than about 35 degrees, or greater than about 40 degrees, or greater than about 50 degrees.

The spray dispenser may be configured to spray the freshening composition at an angle that is between an angle that is parallel to the base of the container and an angle that is perpendicular thereto. The desired size of spray droplets can be delivered by other types of spray dispensers that are capable of being set to provide a narrow range of droplet size. Such other spray dispensers include, but are not limited to: foggers, ultrasonic nebulizers, electrostatic sprayers, and spinning disk sprayers. The spray dispenser may be comprised of various materials, including plastic, metal, glass, or combinations thereof. The spray dispenser may be pressurized, unpressurized or non-aerosol.

A non-aerosol spray dispenser may include a pre-compression trigger sprayer.

One suitable non-aerosol spray dispenser is a plastic non-aerosol dispenser. The dispenser may be constructed of polyethylene such as a high-density polyethylene; polypropylene; polyethyleneterephthalate ("PET"); vinyl acetate, rubber elastomer, and combinations thereof. The spray dispenser may be made of clear PET. Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition. An example of the FLAIROSOL™ dispenser is described in U.S. Pat. No. 8,905,271B2.

A pressurized spray dispenser may include a propellant. Various propellants may be used. The propellant may comprise hydrocarbon(s); compressed gas(es), such as nitrogen, carbon dioxide, air; liquefied gas(es) or hydrofluoro olefin ("HFO"); and mixtures thereof. Preferably, the product comprises a propellant selected from the group consisting of compressed gas such as compressed air, compressed nitrogen, and combinations thereof. Propellants listed in the U.S. Federal Register 30 49 C.F.R. § 1.73.115, Class 2, Division 2.2 are considered acceptable. The propellant may particularly comprise a trans-1,3,3,3-tetrafluoroprop-1-ene, and optionally a CAS number 1645-83-6 gas. Such propellants provide the benefit that they are not flammable, although the freshening compositions are not limited to inflammable propellants. One such propellant is commercially available from Honeywell International of Morristown, N.J. under the trade name HFO-5 1234ze or GWP-6. If desired, the propellant may be condensable. By "condensable", it is meant that the propellant transforms from a gaseous state of matter to a liquid state of matter in the spray dispenser and under the pressures encountered in use. Generally, the highest pressure occurs after the spray dispenser is charged with a freshening composition but before that first dispensing of that freshening composition by the user. A condensable propellant provides the benefit of a flatter depressurization curve as the freshening composition is depleted during usage.

The pressurized spray dispenser may be free of a hydrocarbon propellant. The freshening composition may be delivered from the spray dispenser which includes delivery components including but not limited to a valve to control flow and to seal the freshening composition within the spray dispenser, a button actuator and a nozzle for dispensing the freshening composition to the environment. The freshening composition may be contained in a bag-in-can plastic spray dispenser.

Spray Dispenser

The freshening compositions of the present invention can be contained in plastic containers constructed of hydrophilic perfume compatible materials. These materials avoid complexing, with hydrophilic perfume ingredients, such that absorption by and/or transmission through plastic containers is minimized. Suitable hydrophilic perfume compatible materials can be readily identified by determining the average hydrophilic perfume loss through gas chromatography analysis. Hydrophilic perfume compatible materials result in an average hydrophilic perfume ingredient loss of less than about 50% alternatively less than about 20%, alternatively less than about 15% and alternatively less than about 10% of the originally present individual hydrophilic perfume ingredients.

Freshening compositions containing a substantial amount of hydrophilic perfume ingredients can be stored in plastic container constructed of at least 80% hydrophilic perfume compatible materials for 8 weeks at ambient temperature. After storage, gas chromatography analysis is used to determine the amount of the various perfume ingredients remaining in the aqueous composition and approximate loss is calculated based on the amount of each ingredient originally present.

An effective amount of hydrophilic perfume compatible materials suitable for the present invention is at least about 80%, alternatively about 80% to about 100%, alternatively about 90% to about 100%, and alternatively 100%, by weight of the container. Non-limiting examples of hydrophilic perfume compatible materials are any resins of high density polyethylene (HDPE), low density polyethylene (LDPE), polyvinyl chloride (PVC), polypropylene (PP), polystyrene (PS), polyethylene-co-vinyl alcohol (EVOH), fluorinated polymer such as Aclar®, acrylonitrile-methyl acrylate copolymer such as Barex®, or mixtures thereof. Alternatively HDPE is utilized in the present invention.

In one embodiment, an HDPE bottle, from Plastipak Packaging Inc. Champaign, Ill., is used to contain the aqueous composition of the present invention. HDPE bottles can be made by any blow molding, injection molding, and thermoform process known in the art. For example, for blow molded bottles, heat softened HDPE is extruded as a hollow tube into a mold cavity and forced by pressurized air against the walls of the cold mold cavity to form the bottle. The bottle solidifies by cooling.

It has been found that the perfume compositions having a Clog P of less than about 3 are not fully absorbed into and/or transmitted through the hydrophilic perfume compatible materials such as PP and HDPE. Thus, this assists in preventing transmission of perfume ingredients through plastic containers; which in turn provides consumer noticeable longer lasting fragrance life.

Any of the hydrophilic perfume compatible materials can be used in conjunction with one or more barrier materials including amorphous carbon, silicone oxide or mixtures thereof and metallized coating.

Method of Use

The freshening composition can be used by dispersing, e.g., by placing the freshening composition into a dispenser, such as a spray dispenser and spraying an effective amount into the desired fabric. "Effective amount", when used in connection with the amount of the freshening composition, means an amount sufficient to provide at least a log 2 reduction on the bacteria load present in the area of the fabric treated with the freshening composition. Where delivering a pleasing scent to the fabric in addition to the sanitization benefit, effective amount means an amount sufficient to provide at least about 4 hours, or at least about 6 hours, or at least about 8 hours, or at least about 24 hours of freshness or scent to the treated fabric yet not so much as to saturate or create a pool of liquid on an article or surface and so that, when dry, there is no visual deposit readily discernible. Where malodor reducing ingredients are included, "effective amount", when used in connection with the amount of the freshening composition, means an amount that provides the foregoing and also provides neutralization of a malodor to the point that it is not discernible by the human sense of smell, yet not so much as to saturate or create a pool of liquid on an article or surface and so that, when dry, there is no visual deposit readily discernible. Dispersing can be achieved by using a spray device, a roller, a pad, or other product forms described hereinafter.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

Antibacterial Efficacy (Minimum Biocidal Concentration in Suspension):

The antimicrobial efficacy of the antimicrobial agent in the composition is determined by measuring its Minimum Biocidal Concentration (MBC). The MBC is defined as the lowest absolute concentration of the particular antimicrobial active which provides complete kill (zero bacterial growth). The MBC of the compositions herein was determined against the bacterium, Staphylococcus aureus (S. aureus— ATCC #6538), a gram positive bacterium, and against Escherichia coli (E. coli—ATCC #8739), a gram negative bacterium. These microorganisms are representative of natural contaminants in many consumer and industrial applications. The bacteria inoculum was prepared by transferring several colonies from a Tryptone Soy Agar (TSA) plate to a saline solution (0.85% NaCl), the bacteria concentration in this saline solution was determined by measuring the % Transmittance at 425 nm and adjusted by either adding more bacteria or more saline solution until the % Transmittance at 425 nm was between 23-25% for S. aureus, and between 30-32% for E. coli, this % transmittance corresponds to a bacteria concentration of $10^8$ CFU/ml.

The antimicrobial agent was added to the composition at a level of 3000 ppm, or 1500 ppm, or 750 ppm 200 µL of the fabric refresher composition comprising the antimicrobial agent was dosed into one well of row A of a 96 well microtiter plate. Each subsequent well (rows B to G) were dosed with 100 µL of the same fabric refresher composition, without the addition of the antimicrobial agent. 100 µL of the fabric refresher composition comprising the antimicrobial active was transferred from row A to row B and mixed. 100 µL of the composition was then transferred from row B to row C and mixed, and the process repeated to row G. As such, the concentration of the antimicrobial agent underwent two-fold dilution in adjacent wells, while the concentration of the other actives in the fabric refresher composition remained constant across all the wells in the same column.

10 µL of the $10^8$ CFU/ml bacteria suspension in saline was added to wells A to F of the microtiter plate with row G kept as a nil bacteria control. The final volume in each well was 110 µL, except for row G which comprised 100 µL of the fabric refresher composition and no bacteria suspension. Bacterial inoculation to each column was staggered by 30 seconds to allow for equal incubation times in all wells so that the contact time between the bacteria and the antimicrobial active for all samples was 20 mins. After this contact time, 10 µL of each test solution was transferred to 90 µL of neutralizer solution (Modified Letheen Broth+1.5% Polysorbate 80, supplied by BioMérieux) to stop the antimicrobial action of the antimicrobial active matching the stagger of the inoculation. 2 µL of this solution was plated onto a TSA plate matching the stagger of the inoculation so that all samples are exposed to the neutralizer for the same period of time. The plate was incubated at 32.5° C. for 48 h. MBC concentration is taken as the lowest concentration of the antimicrobial active at which no visible colony growth is observed on the TSA plate.

Antibacterial Efficacy on Fabrics

The bactericidal efficacy on fabric surfaces of fabric refresher compositions comprising different antimicrobial agents was determined against the bacterium, Staphylococcus aureus (S. aureus—ATCC #6538). The bacteria inoculum was prepared by transferring several colonies from a Tryptone Soy Agar (TSA) plate to a saline solution (0.85% NaCl) comprising 5% horse serum as additional soil load, the bacteria concentration in this saline solution was determined by measuring the % Transmittance at 425 nm and adjusted by either adding more bacteria or more saline solution until the % Transmittance at 425 nm is between 23-25% which corresponds to a bacteria concentration of $10^8$ CFU/ml.

Fabric carriers, 1 cm×1 cm disks of cotton sterilized by autoclaving, were inoculated with 50 µL of the $10^8$ CFU/ml bacteria inoculum and incubated for 30 mins at 32° C. After this incubation period, fabric carriers were treated with 2.5 ml of different fabric refresher compositions comprising no antimicrobial active (reference), or 0.05% of either bispyridinium alkane (octenidine dihydrochloride) or N-(3-aminopropyl)-N-dodecylpropane-1,3-diamine (Lonzabac 12.30) as antimicrobial actives. The contact time between the bacteria and the fabric refresher composition in each fabric carrier was 10 mins. After this contact time, each fabric carrier was transferred to 10 ml of neutralizer solution (Modified Letheen Broth+1.5% Polysorbate 80, supplied by BioMérieux) to stop the antimicrobial action of the antimicrobial active. The neutralizer tube containing the fabric carrier was vortexed in a Genie 2 vortexer set at speed 10 for 30 seconds. Ten-fold dilutions of the neutralizer + fabric carrier solution were prepared by transferring 100 µL of the neutralizer solution to 900 µL of a saline solution (0.85% NaCl), this solution was further diluted in saline following the same protocol so that serial ten-fold dilutions were obtained. 100 µL of each of the serial dilutions were plated on a TSA plate, plates were incubated at 32° C. for 48 hours, after this incubation time, the number of colonies in each plate was counted. The target dilution used to determine the bactericidal efficacy of the fabric refresher composition was the one delivering 30-300 CFU in the plate, the data reported for each composition is the average of the bacteria number in three plates multiplied by the target dilution.

The log reduction for each antibacterial treatment vs nil antibacterial active reference is the log 10 of the number obtained by dividing the number of colonies recovered from the fabrics treated with the nil antibacterial active reference by the number of colonies recovered from the fabrics treated with the compositions comprising the different antimicrobial actives.

Example 1: Comparison of Antibacterial Efficacy of Bispyridinium Alkane Vs Other Antibacterial Actives in Fabric Freshening Compositions The antibacterial efficacy of the bispyridinium alkane octenidine hydrochloride was compared to that of quaternary ammonium and alkylamine antimicrobial compounds in two fabric freshening compositions. The minimal biocidal concentration (MBC) in suspension of each antibacterial active against a gram positive bacterium (Staphylococcus aureus) and a gram negative bacterium (*Escherichia coli*) was determined at 20 minutes contact time. Results are shown in Table 1.

| Ingredient | Composition 1 (wt %) | Composition 2 (wt %) |
|---|---|---|
| Glycol phenyl ether (1) | 0.000 | 1.000 |
| Ethanol | 3.000 | 2.000 |
| Polyethyleneimine (2) | 0.065 | 0.065 |
| Silicone-based wetting agent (3) | 0.100 | 0.100 |
| Didecyldimethyl ammonium chloride (4) | 0.060 | 0.060 |
| Maleic Acid | 0.060 | 0.060 |
| Citric acid | 0.015 | 0.015 |
| Preservative (5) | 0.015 | 0.015 |
| Water and minors | To 100% | To 100% |

(1) Dowanol EPh6 - Dow
(2) Lupasol HF - BASF
(3) Silwet L-7600 - Momentive
(4) Uniquat 2250 - Lonza
(5) Koralone B-119 - Dupont

TABLE 1

MBC in suspension of bispyridinium alkane vs other antibacterial actives in fabric refresher compositions

| | MBC (ppm) against S. aureus | | MBC (ppm) against E. coli | |
|---|---|---|---|---|
| | Composition 1 | Composition 2 | Composition 1 | Composition 2 |
| Bispyridinium alkane (6) | 125 | 47 | 500 | 250 |
| N-alkyl aminopropyl glycine (7) | 1500 | 1500 | 1500 | 1500 |
| N-(3-aminopropyl)-N-dodecylpropane-1,3-diamine (8) | 3000 | 3000 | 3000 | 3000 |
| N-alkyl dimethyl benzyl ammonium chloride (9) | 375 | Not tested | 3000 | Not tested |
| N-alkyl dimethyl benzyl ammonium chloride (10) | 562.5 | Not tested | 1500 | Not tested |

(6) Octenidine hydrochloride - Tokyo Chemicals
(7) Rewocid® WK30 - Evonik
(8) Lonzabac 12.30 - Lonza
(9) BTC® 824 - Stepan
(10) BTC® 835 - Stepan As can be seen by comparing the minimum biocidal concentration (MBC) of the bispyridinium alkane octenidine dihydrochloride to that of comparative biocides N-alkyl dimethyl benzyl ammonium chloride (BTC®824, and BTC®835), N-(3-aminopropyl)-N-dodecylpropane-1,3-diamine (Lonzabac 12.30), and N-alkyl aminopropyl glycine (Rewocid® WK30), the bispyridinium alkane shows a much lower MBC than any of the comparative biocides in both exemplified compositions 1 and 2, indicating that the antimicrobial efficacy of the bispyridinium alkane in these compositions is much higher than the antimicrobial efficacy of any of the comparative biocides, and that bispyridinium alkanes, such as octenidine hydrochloride, can be used at much lower concentrations than other commonly used antimicrobial actives to provide fabric freshening compositions with very potent antimicrobial efficacy.

Example 2: Comparison of Antibacterial Efficacy on Fabric Surfaces of Fabric Freshening Compositions Comprising Bispyridinium Alkane or Antimicrobial Alkylamine The antimicrobial efficacy of fabric freshening compositions comprising a bispyridinium alkane or an alkylamine as antimicrobial actives was compared on fabric surfaces using *Staphylococcus aureus* as bacteria load. The test was run in the presence of 5% horse serum to stress the system with additional soil load to mimic situations where the fabric refresher will be used to sanitize unwashed fabrics. Results are shown in table 2.

| Ingredient | Composition A* (wt %) | Composition 3 (wt %) | Composition 4 (wt %) |
|---|---|---|---|
| Ethanol | 3.000 | 3.000 | 3.000 |
| Polyethyleneimine (1) | 0.065 | 0.065 | 0.065 |
| Silicone-based wetting agent (2) | 0.100 | 0.100 | 0.100 |
| Didecyldimethyl ammonium chloride (3) | 0.060 | 0.060 | 0.060 |
| Maleic Acid | 0.060 | 0.060 | 0.060 |
| Citric acid | 0.015 | 0.015 | 0.015 |
| Preservative (4) | 0.015 | 0.015 | 0.015 |
| Bispyridinium alkane (5) | | 0.05% | |
| N-(3-aminopropyl)-N-dodecylpropane-1,3-diamine (6) | | | 0.05% |
| Water and minors | To 100% | To 100% | To 100% |

(1) Lupasol HF - BASF
(2) Silwet L-7600 - Momentive
(3) Uniquat 2250 - Lonza
(4) Koralone B-119 - Dupont
(5) Octenidine dihydrochloride (Tokyo Chemicals)
(6) Lonzabac 12.30 (Lonza)

TABLE 2

Antimicrobial efficacy on cotton fabrics of fabric freshening compositions comprising either a bispyridinium alkane or an alkylamine as antimicrobial active

| Composition | Number of bacteria extracted from treated fabrics | Log reduction vs treatment with nil AB reference |
|---|---|---|
| Comparative A* No AB active | $4 \times 10^5$ CFU/ml | REF |
| Composition 3 Octenidine dihydrochloride | No bacteria extracted from fabrics at any of the dilutions tested | At least log 5 |
| Composition 4 Lonzabac 12.30 | $7.2 \times 10^4$ CFU/ml | Log 0.74 |

As can be seen in Table 2, no viable bacteria were recovered from fabrics treated with a fabric freshening composition comprising octenidine, while about $10^4$ CFU/ml could be extracted from fabrics treated with a fabric refresher composition comprising Lonzabac as antimicrobial active. These results show that fabric freshening compositions comprising a bispyridinium alkane, preferably octenidine hydrochloride, have much higher bactericidal efficacy than fabric freshening compositions comprising other antimicrobial actives such as Lonzabac 12. Indeed, very effective fabric sanitization can be provided by spraying the fabrics with a fabric refresher composition comprising very low levels of a bispyridinium alkane.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of freshening and sanitizing a fabric comprising the step of using a fabric freshening product, wherein the fabric freshening product comprises:
    (a) a freshening aqueous liquid composition comprising from about 0.001% to about 1% by weight of the composition of octenidine dihydrochloride, wherein the composition is an aqueous composition comprising from about 90% to about 99.5% by weight of the composition of water, the composition further comprising a perfume, and wherein the composition is a Newtonian fluid; and
    (b) a spray device to produce a spray of said composition;
    wherein the step of using the product comprises spraying a fabric with the composition.

2. The method according to claim 1, wherein the octenidine dihydrochloride is the only antimicrobial active present in the composition.

3. The method according to claim 1, wherein the composition comprises from about 0.0025% to about 0.5% by weight of the composition of the octenidine dihydrochloride.

4. The method according to claim 1, wherein the composition comprises at least 0.001% by weight of the composition of perfume.

5. The method according to claim 1, wherein the perfume comprises at least about 60% by weight of the perfume of perfume raw materials having Clog P greater than 1.0.

6. The method according to claim 1, wherein the composition further comprises less than about 3.5% by weight of the composition of a surfactant selected from the group consisting of: nonionic surfactants, cationic surfactants, amphoteric surfactants, zwitterionic surfactants, and mixtures thereof.

7. The method according to claim 1, wherein the composition further comprises from about 0.01% to about 5% of a solvent by weight of the composition, wherein the solvent is selected from the group consisting of: an alcohol, a polyol and mixtures thereof.

8. The method according to claim 1, wherein the composition further comprises an alkoxylated phenol according to Formula (I):

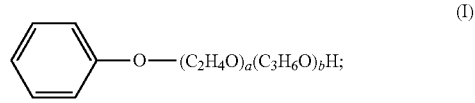

wherein a is a value selected from about 3 to about 15; b is a value selected from about 0 to about 12; wherein the value of a+b, degree of alkoxylation is from about 3 to about 15.

9. The method according to claim 1, wherein the composition further comprises a wetting agent selected from the group consisting of: block co-polymers of ethylene oxide and propylene oxide, block copolymers of silicone, and mixtures thereof.

10. The method according to claim 1, wherein the composition further comprises a setting polymer.

11. The method according to claim 1, wherein the composition further comprises an anti-wrinkle agent.

12. The method according to claim 1, wherein the composition further comprises a malodor counteractant, wherein the malodor counteractant is selected from the group consisting of: polyols, cyclodextrin and derivatives thereof, amine functional polymers, aldehydes, and combinations thereof.

13. The method according to claim 1, further comprising PRMs having ClogP greater than 1 and selected from the group consisting of: dihydro myrcenol, isonoylalcohol, citronellol, tetrahydro linalool, tepinyl acetate, geranyl acetate, phenyl ethyl phenyl acetate, lilial (P. T. Bucinal), vertenex, diphenyl methane, p'cymene, alpha pinene, benzyl salicylate, d-limonene, cis-hexenyl salicylate, hexyl cinnamic aldehyde, cedryl acetate, habanolide, ethyl trimethylcyclopentene butanol, hexyl salicylate, iso e super, ethyl vanillin, helional, undecalactone, ionone gamma methyl, hydroxycitronellal, cyclo galbanate, pyranol, verdox, linalyl acetate, benzyl acetate, methyl phenyl carbinyl acetate, triplal, and mixtures thereof.

14. The method according to claim 1, wherein the composition further comprises a sulfur-containing pro-perfume.

15. The method according to claim 1, wherein the composition further comprises C4-C16 thio-damascone.

16. The method according to claim 1, wherein the spray device is made of plastic, wherein the plastic is selected from the group consisting of: polypropylene, polyethylene terephthalate, high density polyethylene, and combinations thereof.

* * * * *